United States Patent [19]
Bruno

[11] Patent Number: 5,280,177
[45] Date of Patent: Jan. 18, 1994

[54] SAMPLE CELL FOR INFRARED SPECTROPHOTOMETRY

[75] Inventor: Thomas J. Bruno, Broomfield, Colo.

[73] Assignee: The United States of America as represented by the Secretary of Commerce, Washington, D.C.

[21] Appl. No.: 961,286

[22] Filed: Oct. 15, 1992

[51] Int. Cl.⁵ ............................................. G01N 21/03
[52] U.S. Cl. ................................. 250/343; 250/352; 356/246
[58] Field of Search ................. 250/352, 343; 356/246

[56] References Cited

U.S. PATENT DOCUMENTS

| | | | |
|---|---|---|---|
| 2,917,629 | 12/1959 | Andrychuk | 250/304 |
| 3,628,339 | 12/1971 | Porter | 62/5 |
| 4,240,261 | 12/1980 | Inglis | 62/5 |
| 4,825,076 | 4/1989 | Shields | 250/343 |
| 4,869,077 | 9/1989 | Grange et al. | 62/51.1 |
| 4,942,134 | 7/1990 | Winefordner et al. | 436/161 |
| 4,982,089 | 1/1991 | Johnson | 250/304 |

FOREIGN PATENT DOCUMENTS

| | | | |
|---|---|---|---|
| 258093 | 3/1988 | European Pat. Off. | |
| 60-31040 | 2/1985 | Japan | 356/246 |
| 1144408 | 3/1969 | United Kingdom | 356/246 |
| 9011505 | 10/1990 | World Int. Prop. O. | 356/246 |

OTHER PUBLICATIONS

I. M. Dubrovkin, A. S. Sobolev and E. N. Sobolev, "Constant-Thickness Cell for an Infrared Spectrometer." Translated from *Zavodskaya Laboratoriya*, vol. 42, No. 4 (Apr. 1976), p. 428.

Jonathon M. Nash, "Vortex heat exchanger cooling for ir detectors." *Applied Optics*, vol. 14, No. 12 (Dec. 1975) pp. 2911-2913.

*Primary Examiner*—Constantine Hannaher
*Attorney, Agent, or Firm*—Holly D. Kozlowski

[57] ABSTRACT

A sample cell for infrared spectrophotometry comprises a sample holder for holding a sample to be analyzed by infrared spectrophotometry, a cool air passageway and a vortex tube. The sample holder includes a primary optical surface through which infrared radiation is directed to a sample contained in the holder, and the cool air passageway is adjacent the primary optical surface of the sample holder for directing a cool air stream across the primary optical surface. The vortex tube has a cool air outlet connected to the cool air passageway for supplying cool air to the passageway.

11 Claims, 3 Drawing Sheets

SAMPLE CELL FOR INFRARED SPECTROPHOTOMETRY

FIELD OF THE INVENTION

The present invention relates to a sample cell for use in an infrared spectrophotometer. More particularly, the present invention relates to a sample cell for use in an infrared spectrophotometer which includes means for cooling a sample contained therein.

BACKGROUND OF THE INVENTION

In the measurement of infrared (IR) spectra of fluid samples, the fluid sample and the sample cell which contains the sample in the spectrophotometer are heated by the IR radiation. The heating is unavoidable since infrared radiation is essentially heat radiation and as absorption of the radiation occurs, the sample experiences a heating effect. However, it is often desirable to remove heat from the sample during the IR spectrophotometry measurement. For example, liquid volatile solvents and samples which are heated by the IR radiation can vaporize and form bubbles inside a conventional liquid cell, particularly in a continuous-wave instrument. These bubbles cause spiking on the spectrum and usually degrade the spectrum severely before the measurement is complete. In general, better quality spectra are obtained when the sample cell is cooled in some manner.

In other instances, it is often desirable to protect thermally sensitive compounds from excessive heating and resulting degradation during the measurement of their spectra. This is particularly true for natural products and pharmaceuticals wherein infrared spectrophotometry is often used in the study of molecular association. In these studies, the sample cell must be carefully thermostated and the temperature throughout the cell must be uniform in order to minimize experimental error.

The Andrychuk U.S. Pat. No. 2,917,629 discloses an apparatus for infrared analysis of a body of chlorine in a refrigerated cell. The refrigerated cell comprises an open, double walled container in which a refrigerant is circulated between the walls. The device is specific to the measurement of the infrared spectra of liquid chlorine, and lacks application as a multipurpose sample cell. The Johnson U.S. Pat. No. 4,982,089 discloses a method of obtaining the spectra of a product wherein the product is first passed through a gas chromatograph and separated into components, and the resulting components are passed through a chilled region to a spectrometer. The cooling apparatus and method disclosed in these references are both cumbersome and ineffective in avoiding the above-noted heating problems.

Other conventional means for cooling a sample cell for infrared spectrophotometry include commercial thermostats including a cryogenic Dewar flask containing, for example, liquid nitrogen. The thermostat is generally mounted above the sample cell and counterbalance heaters are mounted in the sides of the cell. However, there are several disadvantages associated with these devices. First, the devices are relatively expensive and the cryogenic fluid consumption is high, whereby the small Dewar flask must be frequently refilled. Additionally, the technique of heat balancing with the strip heaters to achieve the desired temperature inevitably leads to undesirable temperature gradients within the cell and sample compartment. The temperature gradients in turn produce density gradients in the liquid samples, thereby preventing the accurate measurement of spectra. Further, there is usually a large and unavoidable heat leak through the windows of the cell, particularly the window closest to the irradiation source, commonly referred to as the entry surface or primary optical surface of the cell. Because the surface area to liquid volume ratio is very high for a sample cell for infrared spectrophotometry, such a heat leak can be very detrimental to the accurate measurement of sample spectra.

Accordingly, a need exists for an improved sample cell for infrared spectrophotometry which accommodates heat removal and temperature control of the sample contained in the cell.

SUMMARY OF THE INVENTION

Accordingly, it is an object of the present invention to provide a sample cell for use in infrared spectrophotometry. It is a more specific object of the invention to provide a sample cell for use in infrared spectrophotometry which conveniently allows for efficient heat removal. It is a further object of the invention to provide a sample cell for use in infrared spectrophotometry which allows a sample contained in the cell to be maintained at an ambient or subambient temperature. It is a related object of the invention to provide an infrared spectrophotometer which includes such a sample cell.

These and additional objects are provided by the sample cell and infrared spectrophotometer according to the present invention. More particularly, the sample cell according to the present invention is adapted for use in infrared spectrophotometry. The sample cell comprises a sample holder for holding a sample to be analyzed by infrared spectrophotometry. The sample holder includes a primary optical surface through which infrared radiation is directed to a sample contained in the holder. The sample cell further comprises a cool air passageway adjacent the primary optical surface of the sample holder for directing a cool air stream across the primary optical surface, and a vortex tube having a cool air outlet in communication with or connected to the cool air passageway for supplying cool air to the passageway. The infrared spectrophotometer according to the present invention includes such a sample cell, means for directing infrared radiation to a sample contained in the cell and means for measuring a spectra resulting from irradiation of a sample contained in the sample cell.

The sample cell and infrared spectrophotometer according to the present invention are advantageous in that they allow cooling of the sample contained in the cell to temperatures as low as $-40°$ C. As will be set forth in detail below, the sample cell is relatively inexpensive while providing efficient cooling of samples contained therein before and during IR spectra measurements. The present cell is further advantageous in that it does not require a cryogenic liquid or a power supply for counterbalance heaters. Moreover, the sample cell is advantageous in that the cooling medium, i.e. the cold air supplied by the vortex tube, does not interfere with or absorb infrared radiation.

These and additional objects and advantages provided by the sample cell and infrared spectrophotometer according to the present invention will be more fully apparent in view of the following detailed description.

DETAILED DESCRIPTION

The sample cell according to the present invention is particularly adapted for use in infrared spectrophotometry. The sample cell comprises a sample holder for holding a sample to be analyzed by infrared spectrophotometry. The sample holder includes a primary optical surface through which infrared radiation is directed to a sample contained in the holder. The sample cell further includes a cool air passageway adjacent the primary optical surface of the sample holder for directing a cool air stream across the primary optical surface, and a vortex tube having a cool air outlet in communication with the cool air passageway for supplying cool air to the passageway.

Figure 1:
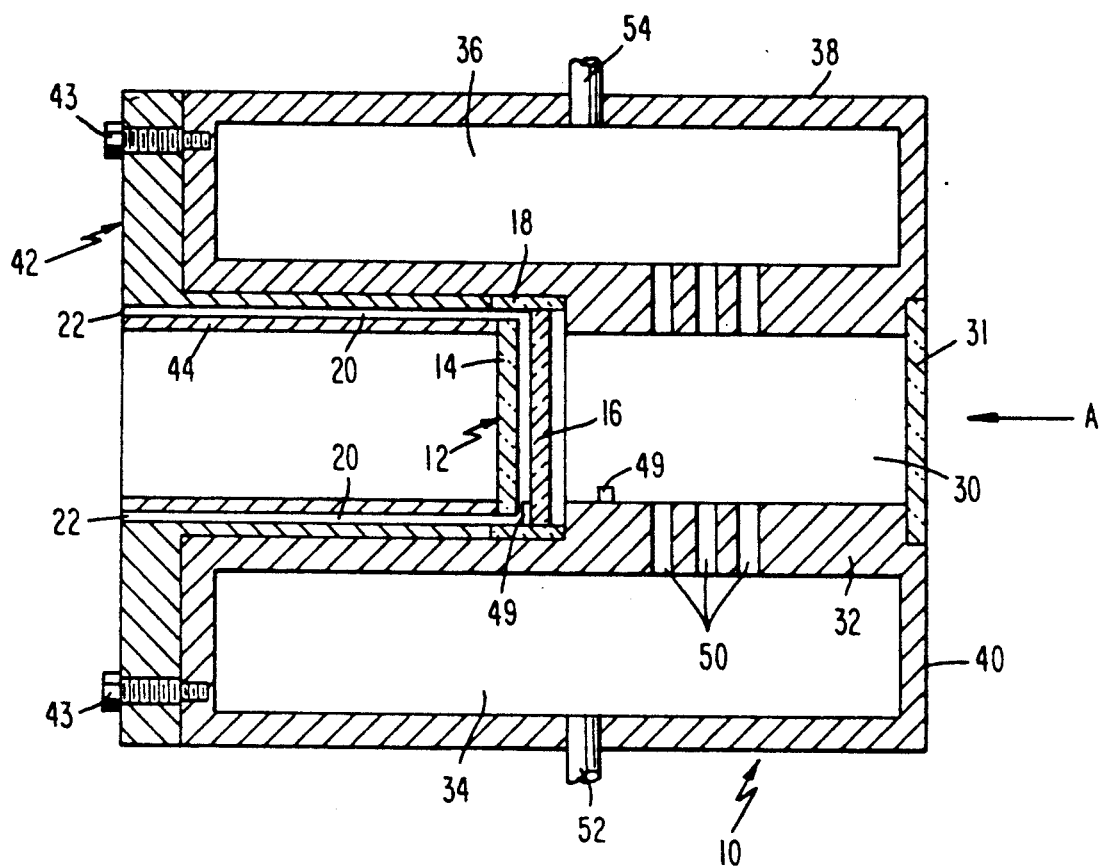
FIG. 1 sets forth a schematic diagram of one embodiment of the sample cell according to the present invention, excluding the vortex tube.
Figure 2:
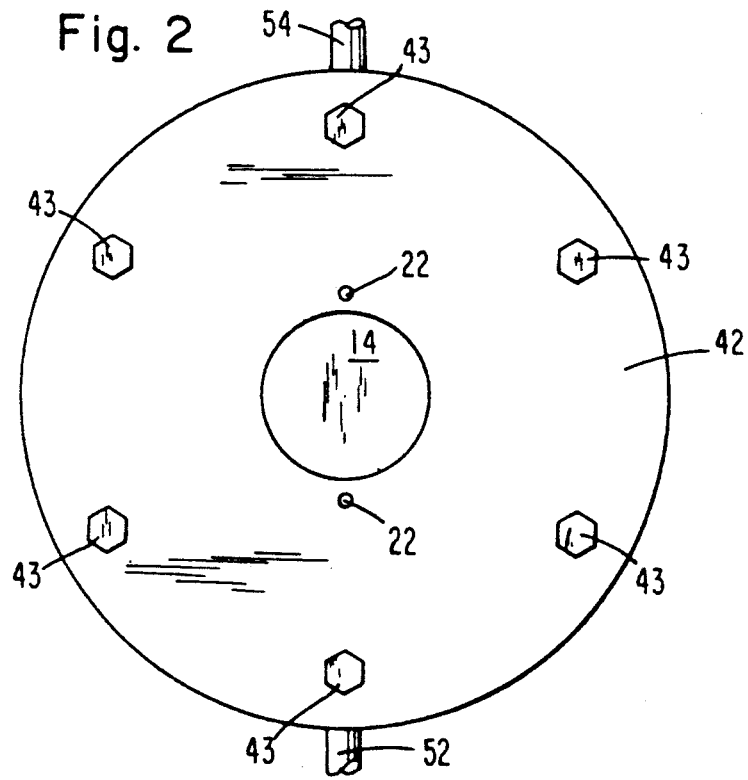
FIG. 2 is a top view of one end of the sample cell shown in FIG. 1.

One embodiment of the sample cell according to the present invention is set forth in FIG. 1. With reference to FIG. 1, the sample cell 10 includes a sample holder 12 for holding a sample to be analyzed by infrared spectrophotometry. The sample holder 12 is formed from a pair of salt plates 14, 16 arranged in spaced relation to one another with a fluid tight spacer 18 therebetween. The cell plates may conveniently be formed of sodium chloride (salt). The sample cell 10 in FIG. 1 is designed to receive infrared radiation in the direction indicated by arrow A, whereby the salt plate 16 serves as the primary optical surface through which infrared radiation is directed to a sample contained in the sample holder. A fluid tight spacer 18 is arranged between the salt plates 14 and 16 which form the sample holder 12 and may be formed of any suitable material, for example polytetrafluoroethylene (PTFE). Additionally, the outermost surfaces of the salt plates may be provided with additional PTFE sealing gaskets to hold the plates in sealing engagement. A thrust ring 42 is held in place with threaded fasteners 43 to provide the compression necessary to achieve sealing engagement of the salt plates and the PTFE spacers, as shown in FIG. 2, and as described in further detail below.

Preferably, the salt plate which is opposite the primary optical surface, and the sealing gasket of this plate, if provided, contain at least one small inlet through which a fluid sample may be injected into the interior of the sample holder. The sample cell 10 shown in FIG. 1 includes two such inlets 20 in the salt plate 14. The inlets 20 may be of any appropriate diameter, for example about 0.03 cm in diameter is suitable. In a preferred embodiment, two inlets are provided, and the inlets are within about 1.5 mm of the edge of the salt plate and are located at 180° from one another.

Liquid sample may be directed to the respective inlets 20 of the sample holder by means of a syringe placed in the corresponding syringe guides 22. As set forth in the embodiment of FIG. 1, each inlet 20 to the sample holder is provided with a syringe guide 22 for syringe application of a liquid sample thereto. In the embodiment of FIG. 1, a third concentric tube 44 extends from the outer thrust ring 42 and contains the syringe guides 22. When the inlets 20 and the guides 22 are not in use, they may be plugged with rods or the like, formed, for example, of PTFE.

The sample cell further includes a cool air passageway adjacent the primary optical surface of the sample holder for directing a cool air stream across the primary optical surface. In the embodiment of the sample cell shown in FIG. 1, the cool air passageway is indicated by reference numeral 30. The cool air passageway may be formed of any suitable material, including metal, plastic or glass. In the embodiment shown in FIG. 1, the cool air passageway 30 is formed of a thin-walled stainless steel tubing 32. As is evident from FIG. 1, the cool air passageway 30 is adjacent the primary optical surface 16 of the sample holder and therefore allows cool air to pass directly across the primary optical surface, thereby providing efficient cooling of the sample holder and a sample liquid contained therein. As shown in FIG. 1, the cool air passageway 30 includes a salt plate 31 through which infrared radiation passes to the primary optical surface 16 of the sample holder 12. In a preferred embodiment, the cool air passageway 30 extends along sides of the sample holder which are adjacent the primary optical surface. As shown in the embodiment of FIG. 1, the cool air passageway extends along the sides of the sample holder at 34 and 36, respectively. A larger concentric thin-walled stainless steel tubing 38 may be used to form the extended passageway at 34 and 36. Stainless steel tubings 32 and 38 may be connected by any suitable means, for example stainless steel end plates or thrust rings 40, 42 as shown in FIG. 1. When the passageways are formed of stainless steel tubing as shown in FIG. 1, the concentric tubings and end plates may be attached by threaded fasteners, welding, brazing or like means as will be apparent to those skilled in the art.

Figure 4:
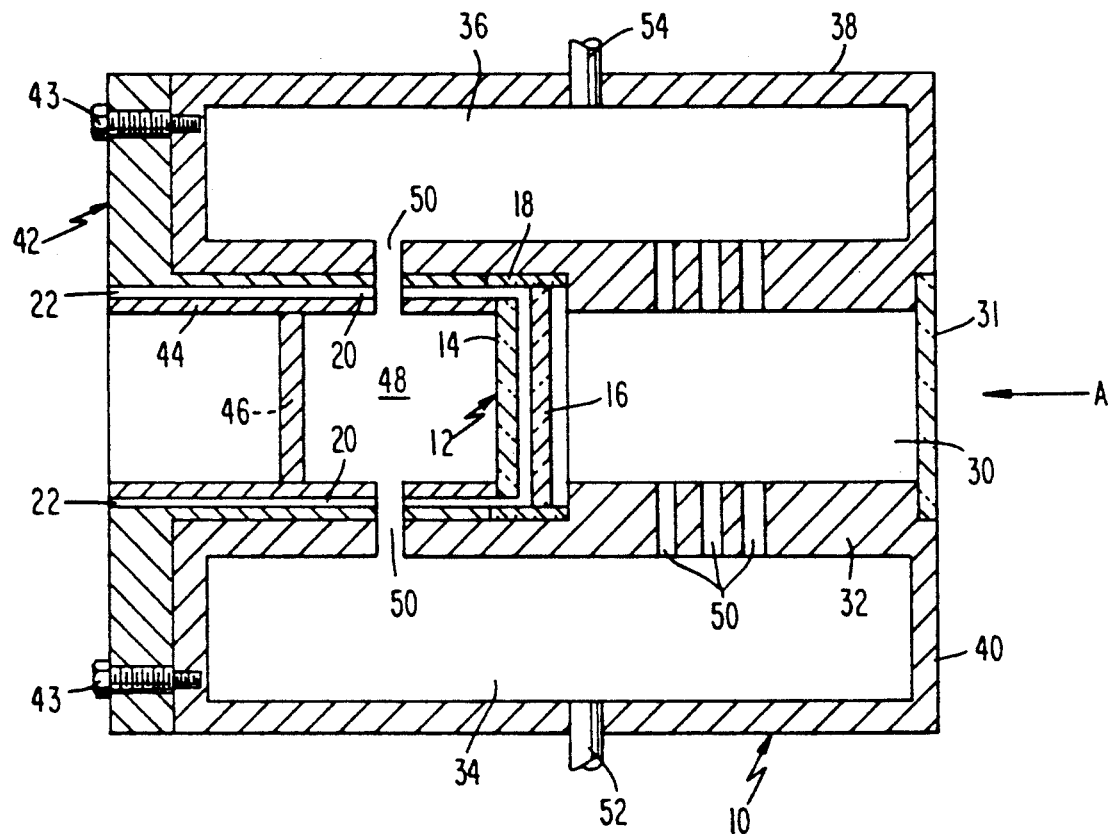
FIG. 4 sets forth a schematic diagram of a second embodiment of the sample cell according to the present invention, excluding the vortex tube.

In a further embodiment shown in FIG. 4, the cool air passageway may extend along the entire perimeter of the sample holder. For example, a further end wall 46 may be included to provide a further extension 48 of the cool air passageway 30 across salt plate 14 of the sample cell. The extensions 34, 36 and 48 of the cool air passageway 30 may all be connected by means of vents or the like of the type indicated generally by reference numeral 50.

The cool air passageway is provided with an inlet 52 and an outlet 54 for the entrance and exit of the cooling air. In accordance with an important feature of the invention, the cool air supply is provided by a vortex tube which is in communication with the cool air inlet 52. Vortex tubes are known in the art and are available commercially in a number of sizes. See, for example, Hillsch, R., *Rev. Sci. Instr.*, 1947, 18(2), 108; Blaber, M. P., *J. Sci. Instr.*, 1950, 27(6), 1968; Blatt, T. A., et al, ASME Paper 62-WA-200, 1963; Vortec Corporation, *A Short Course on Vortex Tubes and Application Notes*, 1984; Comassar, S., *J. Am. Soc. Naval Engrs.*, 1951, 63:1, pp. 99–108; Aronson, *Machine Design*, Dec. 9, 1976, all of which are incorporated herein by reference.

Figure 3:
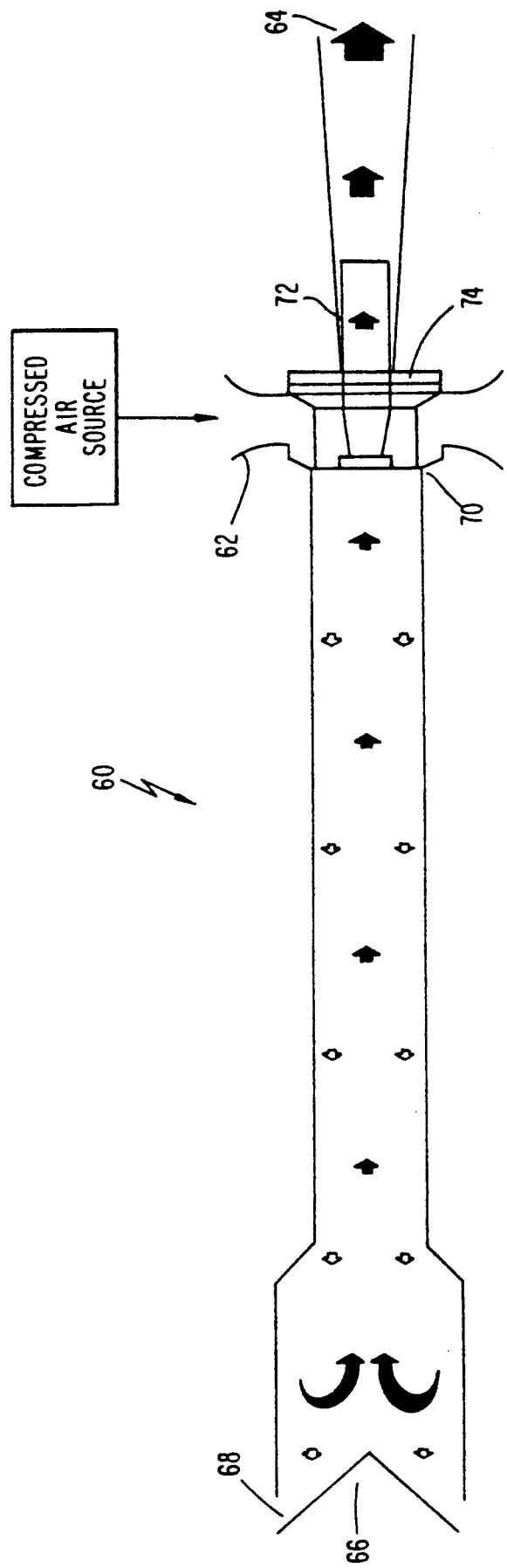
FIG. 3 sets forth a schematic diagram of the vortex tube which is included in the sample cell of the present invention.

A suitable vortex tube for use in the present invention is shown schematically in FIG. 3. The vortex tube 60 includes a compressed air inlet nozzle 62, a cold air outlet 64 and a hot air outlet 66. The hot air outlet is provided with a control valve 68 in order to control the flow of hot air from the vortex tube. The vortex tube includes the vortex generation chamber indicated generally by reference numeral 70 containing a vortex generator 72. A diaphragm 74 is also included in the vortex tube in a manner well known in the art. As is also known in the art, the vortex generator may comprise a replaceable insert with different vortex generator inserts being used to adjust the temperatures of air provided at the hot and cold outlets, respectively. Generally, vortex tubes can provide cold air at a temperature as low as $-40°$ C. and hot air at a temperature as high as $200°$ C. The hot and cold outlet temperatures can be adjusted by use of the hot air outlet control valve 68 and/or by replaceable inserts in the vortex generator 72.

In the present apparatus, the cold air outlet 64 of the vortex tube 60 is in communication with the cool air inlet 52 of the passageway 30 and thereby provides cool air throughout the passageway for cooling the sample holder and sample contained therein. The apparatus of the present invention is particularly advantageous since the cool air passageway extends adjacent the primary optical surface of the sample holder through which infrared radiation passes and which exhibits extensive heating in conventional sample cells. In the present apparatus, the cold air from the vortex tube is in thermally responsive relation with the primary optical surface of the sample holder, thereby providing efficient cooling of the sample cell and a sample contained in the cell.

The vortex tube is advantageous for use in the present apparatus in that a compressed air inlet supply is the only requirement for operation of the vortex tube. Any suitable compressed air supply may be used for operation of the vortex tube in accordance with known vortex tube operation.

Figure 5:
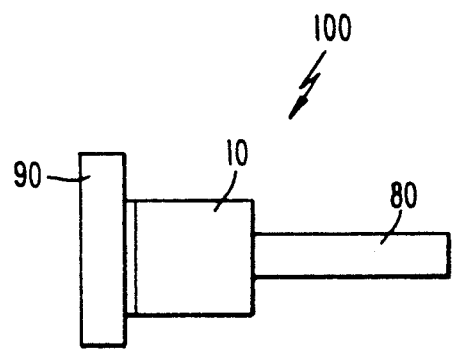
FIG. 5 sets forth a schematic diagram of an infrared spectrophotometer of the present invention.

The sample cell according to the present invention is used in an infrared spectrophotometer in combination with means for directing infrared radiation to a sample contained in the sample cell and means for measuring spectra resulting from irradiation of a sample contained in the sample cell, in accordance with conventional spectrophotometer apparatus. For example, FIG. 5 sets forth a schematic diagram of an infrared spectrophotometer 100 including means 80 for directing infrared radiation to a sample contained in sample cell 10 according to the invention and means 90 for measuring spectra resulting from irradiation of a sample in the sample cell. Depending on the particular spectrophotometer with which the sample cell is to be used, the sample cell may include means for suitable mounting of the cell in the spectrophotometer. Such means will be apparent to one of ordinary skill in the art and dependent on the particular spectrophotometer apparatus design with which the sample cell is used.

In operation, the sample cell is removed from the spectrophotometer to load a liquid sample into the sample holder via a syringe guide 22 and a sample inlet 20. Either before or after the sample cell is replaced in the spectrophotometer, depending on the accessibility of the sample cell in the spectrophotometer, the cold outlet of the vortex tube 60 is connected with the cool air inlet 52 of the passageway 30. Plastic tubing or the like may be used for connecting the cold air outlet of the vortex tube with the cool air inlet 52 of the passageway. In a preferred embodiment, the tubing is provided with an insulating jacket formed of glass fiber or the like. The vortex tube is then pressurized with a compressed air supply and cold air is directed to the cool air passageway 30. The temperature of the air may be as low as $-40°$ C. Temperatures between ambient and this lower level may be obtained by adjusting the control valve of the vortex tube and/or by use of different vortex generators. Generally, the cool air temperature from the vortex tube may be controlled to within $1°$ C., $\pm 0.5°$ C. A thermocouple or any other temperature measurement means may be placed in the cool air passageway and/or the sample holder in order to measure the sample cell temperature. For example, as shown in FIG. 1, a thermocouple 49 may be placed in the cool air passageway 30 and/or in the sample holder 12. As will be apparent to one of ordinary skill in the art, the cold air from the vortex tube may be directed to the cool air passageway 30 prior to loading the sample in the sample holder if so desired.

The sample cell according to the present invention is advantageous in that it may be constructed from relatively inexpensive materials and that it does not require any cryogenic liquids or counterbalance heaters. The apparatus is further advantageous in that cool air is applied directly to the primary optical surface, thereby efficiently cooling the sample holder and liquid sample contained therein. Additionally, the cool air will not absorb the infrared radiation as the radiation passes through the cool air passageway to the primary optical surface. Moreover, the cool air will not attenuate the infrared radiation to any further extent than is already caused by the sample compartment path length of the spectrophotometer.

A sample cell as shown in FIG. 1 has been used to obtain infrared spectra on a series of very volatile fluids which are being studied as alternative refrigerants wherein it is important to obtain the spectrum in the liquid phase. The present sample cell has maintained samples in the condensed liquid phase, even under the influence of the infrared radiation beam. As noted previously, the present apparatus is further advantageous in preventing thermal decomposition or degradation of thermally sensitive samples.

The preceding specific embodiments are set forth to illustrate the invention and are not intended to limit the scope of the apparatus of the present invention. Additional embodiments and advantages within the scope of the claimed invention will be apparent to one of ordinary skill in the art.

What is claimed is:

1. A sample cell for infrared spectrophotometry, comprising a sample holder for holding a sample to be analyzed by infrared spectrophotometry, the sample holder including a primary optical surface through which infrared radiation is directed to a sample contained in the holder, a cool air passageway adjacent the primary optical surface of the sample holder for directing a cool air stream across the primary optical surface, and a vortex tube having a cool air outlet connected to the cool air passageway for supplying cool air to the passageway.

2. A sample cell as defined by claim 1, wherein the sample holder comprises a pair of salt plates arranged in spaced relation to one another with a fluid tight spacer therebetween, and wherein one of the salt plates is the primary optical surface.

3. A sample cell as defined by claim 2, wherein the sample holder further comprises a sample inlet.

4. A sample cell as defined by claim 1, wherein the cool air passageway includes a salt plate through which infrared radiation passes to the primary optical surface of the sample holder.

5. A sample cell as defined by claim 1, wherein the cool air passageway extends along sides of the sample holder which are adjacent the primary optical surface.

6. A sample cell as defined by claim 1, wherein the cool air passageway extends along the entire perimeter of the sample holder.

7. A sample cell as defined by claim 1, wherein the cool air passageway includes an air inlet connected with the cool air outlet of the vortex, and an air outlet.

8. A sample cell as defined by claim 1, wherein the vortex tube is supplied with a compressed air inlet stream.

9. A sample cell as defined by claim 1, further including a temperature measuring means arranged in the cool air passageway.

10. A sample cell as defined by claim 1, further including a temperature measuring means arranged in the sample holder.

11. An infrared spectrophotometer, including a sample cell, means for directing infrared radiation to a sample contained in the sample cell, and means for measuring spectra resulting from infrared irradiation of a sample contained in the sample cell, wherein the sample cell comprises a sample holder for holding a sample to be analyzed by infrared spectrophotometry, the sample holder including a primary optical surface through which infrared radiation is directed to a sample contained in the holder, a cool air passageway adjacent the primary optical surface of the sample holder for directing a cool air stream across the primary optical surface, and a vortex tube having a cool air outlet connected to the cool air passageway for supplying cool air to the passageway.

* * * * *